United States Patent [19]

Schomburg et al.

[11] Patent Number: 5,502,169
[45] Date of Patent: Mar. 26, 1996

[54] DEACTIVATION OF THE INNER SURFACES OF CAPILLARIES

[75] Inventors: Gerhard Schomburg; Martin Gilges, both of Mülheim an der Ruhr, Germany

[73] Assignee: Studiengesellschaft Kohle mBH, Mulheim an der Ruhr, Germany

[21] Appl. No.: 344,200

[22] Filed: Nov. 23, 1994

Related U.S. Application Data

[63] Continuation of Ser. No. 118,911, Sep. 9, 1993, abandoned.

[30] Foreign Application Priority Data

Sep. 11, 1992 [DE] Germany .......................... 42 30 403.2

[51] Int. Cl.[6] .............................. C07K 1/14; C07K 1/26; C25D 13/06; C07H 21/00
[52] U.S. Cl. .......... 204/454; 530/344; 530/412; 536/22.1; 204/455; 204/601; 204/605
[58] Field of Search ...................................... 530/412, 344; 536/22.1, 26, 27, 28.4, 29.1; 204/180.1, 180.2, 180.7, 182.8

[56] References Cited

U.S. PATENT DOCUMENTS

| | | | |
|---|---|---|---|
| 4,680,201 | 7/1987 | Hjerten | 427/230 |
| 4,865,707 | 9/1989 | Karger et al. | 204/182.8 |
| 4,997,537 | 3/1991 | Karger et al. | 204/182.8 |
| 5,221,447 | 6/1993 | Hjerten | 204/180.1 |
| 5,282,941 | 2/1994 | Rose | 204/182.8 |

FOREIGN PATENT DOCUMENTS 1233907  4/1968  United Kingdom.

OTHER PUBLICATIONS

Hjerten "Free Zone Electrophoresis" Chromatog. Rev. 9 122–219 1967.
Journal of High Resolution Chromatography and Chromatography Communications, vol. 15, No. 7, Jul. 1992, Heidelberg De, pp. 452–457, M. Gilges, et al.
Journal of Chromatography, vol. 477, No. 1, Aug. 1989, pp. 63–71, P. Sandra et al.
Schoncich et al. "Separation Analysis of Peptides & Proteins", Anal. Chem. 65:67R–84R, 1993.
Anal. Chem. 1992, 64, pp. 2665–2671.

Primary Examiner—Michael G. Wityshyn
Assistant Examiner—Nancy J. Degen
Attorney, Agent, or Firm—Sprung Horn Kramer & Woods

[57] ABSTRACT

The invention relates to a process for deactivating the inner surfaces of capillaries for capillary zone electrophoresis and capillary gel electrophoresis. The deactivation is effected by coating the inner surface with polar polymers which initially are water-soluble, whereupon the polymers are subsequently thermally fixed by a formation of water-insoluble polymers. The invention further relates to the capillaries thus produced and to the use thereof for the separation of oligonucleotides, peptides and proteins.

12 Claims, 9 Drawing Sheets

$R_1 = R_3 = CH_3 \quad R_2 = H$

1: $R_1 = R_2 = H$    $R_3 = CH_3$
2: $R_2 = R_3 = CH_3$    $R_1 = H$

DEACTIVATION OF THE INNER SURFACES OF CAPILLARIES

This application is a continuation of application Ser. No. 08/118,911, filed Sep. 9, 1993, now abandoned.

The invention relates to a process for deactivating the inner surfaces of capillaries for capillary zone electrophoresis and capillary gel electrophoresis, to the capillaries obtained thereby and to the use thereof for the separation of oligonucleotides, peptides and proteins.

In the CZE ("capillary zone electrophoresis") variant of modern capillary electrophoresis (CE), but also, e.g., in capillary gel electrophoresis (CGE), capillaries made of "fused silica" (FS) material are virtually exclusively used. These capillaries, without or with a pretreatment of the inner surface, are filled with buffer solutions. A strong electric field (<60 kV/m) is applied to the ends of the capillary which are immersed, together with the electrodes, in buffer vessels. Electrophoretic separations occur under the influence of the electric field established in the capillary filling, said separations being caused by the different electromobilities of charged analyte molecules. Capillaries made of "fused silica" material first have been virtually exclusively used in CE, because they are mechanically flexible and are commercially available having those narrow diameters as required (<100 μm). Because of the low wall thickness and the nature of the material (quartz), they allow a good removal of heat to be accomplished which is generated in the buffer by the current flowing in the buffer depending on the ionic strength thereof.

The acidic surface properties of such capillaries ensue from silanol groups present thereon. They affect capillary electrophoretic separations in various ways to such a degree that in analytical practice good and reproducible separations cannot be accomplished, unless these surfaces have been appropriately modified. The pH value of the buffer affects the dissociation of the silanol groups which may be present in varying concentrations, depending on the process of manufacture and also on the pretreatment (such as by etching).

The surfaces, upon contact with the buffers, will be negatively charged depending on the pretreatment and, in accordance with generally accepted theoretical considerations, ζ-potentials are established which result in an electroosmotic flow (EOF) in the buffer under the action of the electric field. Said EOF may be effective into the same direction as the electromigration, but also into the opposite direction. The transportation through the capillary of the analyte molecules to be separated may be accelerated or retarded by modifying the surface properties.

However, the surfaces of the capillaries, because of their charge as well as quite generally because of their adsorptive property, cause intermolecular interactions between the analyte molecules and the wall to occur, which interactions adversely affect the separation procedure and result in a change in migration times and, more particularly, due to a broadening or distortion of bands, and consequently in a very strong and disadvantageous deterioration of the separation efficiency and, hence, resolution.

In CE, such interactions are absolutely undesirable for achieving good i.e. highly efficient analytical separation, differently from what is common in liquid chromatography (LC).

Thus, the separation properties of capillaries for electrophoresis are largely affected by the condition of the inner surfaces. Since it is of analytical interest to change the magnitude of the EOF, or even its direction, processes for modifying the surfaces by way of adsorption or chemical bonding of small and large (oligomeric or even polymeric) molecules are a subject matter of great practical interest. However, it is indispensably necessary, that the modification of the surface will not result in an increase in the adsorptivity of the surfaces for the analyte molecules to be separated so that good, i.e. efficient, separations with high resolution would become impossible. This is quite particularly applicable to the separation of oligonucleotides, peptides and proteins which, depending on the structures and conformations thereof, will undergo hydrophobic or hydrophilic intermolecular interactions with the surfaces.

Various processes for modifying the surfaces in capillary electrophoresis and capillary gel electrophoresis have been known in the art, and so have been the drawbacks thereof: Change in the pH value and in the ionic strength of the buffer and, thus, in the degree of ionization of the silanol groups.

Thereby, also the charge of the acidic or basic analytes and, hence, the electromobilities thereof, may be changed. With view to separations of proteins, a sufficient surface deactivation can be accomplished only by using extreme pH values, at which, however, many proteins are not stable any more. The use of high ionic strengths in the buffer is limited by the strong heat development due to the increased electric current flow.

Addition of modifying agents at low concentrations to the working buffers.

These are adsorbed on the surfaces and change the properties thereof with respect to EOF and analyte adsorption. The adsorption of such additives is much dependent on the nature of the capillary surface which is affected by the mostly unknown procedures of manufacture by different producers and by the history and/or pretreatment of the capillary.

Derivatization of the surfaces by silanization.

This type of reactions provides two effects. Part of the acidic silanol groups is removed from the surface and, by means of a suitable substitution of the silanizing reagent, there is provided the possibility of fixing smaller or larger or even polymeric molecules onto the inner surfaces of the capillaries. The interaction thereof with analyte molecules should be very low or absent at all. Coatings can be prepared which have hydrophobic or hydrophilic or even ionic properties. Surface coatings comprising polymers which are stable when the capillary has been filled with the buffers as typical for CE, may be fixed also just by way of adsorption. This is possible, more specifically, if, on the one hand, the polymers are strongly polar and, on the other hand, are very sparingly soluble or even insoluble in the aqueous buffers of the different pH values. Coatings with polar or nonpolar polymers (e.g. polyethyleneglycols) such as those used in capillary gas chromatography have proven to be not suitable for reproducible measurements in series and for separations of proteins at higher pH values. A particular difficulty is encountered, if hydrophilic, optionally hydroxylic, also larger molecules are to be fixed to the surfaces, because said molecules, due to the polarities thereof, are very well soluble in the aqueous buffers. For this reason it has been attempted in various approaches to attach hydrophilic molecules or molecule groups to the surface by way of chemical bonds after preceding silanization using bifunctional reagents {S. Hjert+n, J. Chromatogr. 347 (1985) 191; G. M. Bruin, J. P. Chang, R. H. Kuhlmann, K. Zegers, J. C. Kraak and H. Poppe, J. Chromatogr. 471 (1989) 429; and K. A. Cobb, V. Dolnik and M. Novotny; Anal. Chem. 62 (1990) 2478}.

The known methods of silanol derivatization are troublesome and time-consuming. As far as the reproducibility thereof is concerned, they depend on the respective manufacturing process and/or on the selected pretreatment of the capillary, e.g. by etching. Such surface modifications in CE capillaries are not stable over some larger pH range with respect to influencing the EOF and suppressing the analyte adsorption, because the covalent bond through Si—O—Si linkages of the modifying molecules is attacked, especially at higher pH values.

Surfaces that have been silylated with alkyl-substituted silanes are too hydrophobic for a protein separation and result in an adsorption of these proteins and the denaturation thereof. Other simple silylations also employing reagents which contain polar substituents do not produce a sufficient deactivation. However, more particularly, hydroxylically modified surfaces such as those prepared, e.g., by J. K. Towns and F. E. Regnier, Anal. Chem. 63 (1991) 1126, in an expensive multi-step process by adsorption of detergents on hydrophobic, e.g. $C_8$-silanized surfaces, were usable for separations of proteins. The capillaries thus prepared were suitable for carrying out efficient protein separations also at higher pH values (up to 7). Other capillaries (e.g. according to Poppe, loc. cit.) failed to still provide a good resolution of the proteins already at pH values of >4, supposedly because of adsorption.

In general there applies the following: One important criterion of good capillaries for the separation of various basic and acidic proteins is the pH range within which the proteins can be eluted at all and within which the modifications are stable.

With respect to the covalent bond of coatings through Si—O—Si linkages there is to be taken into consideration that these are not stable over the whole pH range, and more specificly so not at a pH >7. Nevertheless, at higher pH values the silica backbone will also be attacked, especially so, if the surface has not been well covered or shielded. Surface modification by adsorption of polar systems.

The process described by M. Gilges, H. Husmann, M.-H. Kleemiβ, St.R. Motsch and G. Schomburg, HRC 15 (1992) 452, of the dynamic surface modification with polyvinyl alcohol (PVA) as a buffer additive in CZE could be utilized for the separation of proteins and/or of chiral basic smaller molecules. Protein separations could be effected in such systems only at pH values of <4. However, in series using PVA as a buffer additive, after only one analysis or just a few analyses it was required to replace the filling of the capillary with fresh buffer after some intermediate step of flushing with pure water.

The solubility in water of polyvinyl alcohols is strongly reduced by a thermal treatment at temperatures of up to 180° C. due to the formation of semicrystalline highly associated structures {Encyclopedia of Polymer Science and Engineering, Vol. 17, John Wiley & Sons, Inc., New York, 1989; and J. F. Kenney and G. W. Willcockson, J. Polymer Sci. A-1, 4 (1966) 679}.

In JP-92-053191 there has been described a carrier for electrophoresis of proteins. Said carrier comprises a temperature-sensitive high-polymer compound having a low critical dissolution temperature, which compound has been selected from a poly-N-substituted acrylamide derivative, a poly-N-substituted methacrylamide derivative, or a copolymer thereof, polyvinylmethylether and partially oxidized polyvinyl alcohol.

The instability of capillaries as produced by means of a silanization in most of the processes used hitherto, however, makes it impossible to conduct separations in series with a reproducible migration behavior. The drawback inherent to the dynamic surface modification consists of that the coating will have to be renewed after one or several separation(s).

Accordingly, it is the object of the present invention to produce stable capillaries which, more specifically, are suitable for conducting serial separations with a reproducible migration behavior.

In a first embodiment of the present invention said object is attained by a process for deactivating the inner surface of capillaries for capillary zone electrophoresis and capillary gel electrophoresis by coating said inner surface with polar polymers which initially are water-soluble, whereupon the polymers are subsequently thermally fixed by a formation of water-insoluble polymers.

By means of the present invention it could be demonstrated that capillary surfaces can be coated with thermally fixed polymers and that such capillaries are capable of avoiding the above-described drawbacks of prior art.

By means of the process according to the invention it is possible to form semi-crystalline highly associated structures of the polymers on the surfaces so that these polymers lose their initial solubility in water. This is why also in a series of separations a renewal of the surface coating is not necessary.

In a preferred embodiment of the present invention there are employed capillaries made of amorphous molten silicon dioxide which are obtained from silicagel or hydrolyzed silicon tetrachloride. These are commonly designated also as "fused silica" materials.

A particularly preferred water-soluble polymer within the scope of the present invention is polyvinyl alcohol (PVA) which is commercially available in various degrees of hydrolysis and having a variety of molecular weights. It is preferred to employ polyvinyl alcohol in the form of an aqueous solution which contains from 0.1 to 20% by weight, especially from 0.5 to 10% by weight. The amount to be employed is per se not critical as long as the total amount of polyvinyl alcohol is sufficient to ensure a uniform covering as dense as possible of the surface of the capillary. In order to prepare capillary columns having, if possible, the same separation efficiency it is of course required to choose equal amounts of polyvinyl alcohol in each case.

Within the scope of the present invention the aqueous solution of the polymers is first introduced into the capillary. Within the scope of the present invention it is preferred to drain the capillary column by applying an elevated pressure thereto. It is only thereafter that the thermal fixation of the polymers is effected.

In order to produce the semi-crystalline highly associated structures it is necessary to heat the capillary at an elevated temperature. It is preferred that the temperature range is in excess of the boiling point of water under the selected pressure conditions, whereby the fixation is carried out optionally under an inert gas, for example nitrogen.

Preferably, the thermal fixation of the water-soluble polymers is accomplished by heating the capillaries under atmospheric pressure or a slightly reduced pressure at a temperature within the range of from 100° C. to 250° C., especially from 130° C. to 180° C., for a period of from 0.5 to 24 hours, and especially from 1 to 12 hours. If the selected fixation temperature is too high, then one has to be afraid of a thermal degradation of the polymer (polyvinyl alcohol). If, in contrast thereto, the selected temperature is too low, then the solvent water cannot evaporate in a sufficient amount, and the semi-crystalline highly associated structures will not be formed. In a similar manner the duration of the thermal fixation is important. During the fixation it is preferred within the scope of the invention to pass an inert gas, for example nitrogen or argon, through the capillary so that the polymers can be prevented from undergoing an oxidative degradation.

One further embodiment according to the invention consists of the capillaries for capillary zone electrophoresis and capillary gel electrophoresis obtainable by the process as defined above.

The capillaries thus produced may be used for a variety of analytical purposes. It is particularly preferred that the capillaries are used for the separation of oligonucleotides, peptides and proteins. Thus, in this area, more specifically, difficult separation problems can be readily solved by means of the capillaries according to the invention. In a particular manner the capillaries according to the invention are usable for repeated separations, since here a very high reproducibility is achieved, several hundred separations of various proteins could be performed at a pH of 3 to 10 without changes in migration times and peak width or symmetry.

While a major portion of the conventional capillaries as known in prior art is usable only within extreme, i.e. strongly acidic, pH ranges, it is possible by means of the present invention to carry out even repeated several hundred separations of proteins within a pH range of from 3 to 10, preferably 3 to 7 and more preferably from 5.5 to 7 with a high reproducibility.

The capillaries obtainable according to the invention have been permanently coated with water-insoluble PVA and could be used for analytic separations without any particular conditioning treatment. Series of protein separations could be carried out using capillaries having an effective length of, for example, 57 cm also at average pH values of from 5 to 7 with a high efficiency (up to 1,200,000 theoretical plates per meter) and with a good reproducibility of the migration times of the test proteins employed. Herein no PVA was added to the buffer.

These capillaries do not exhibit the drawbacks inherent to those prepared in accordance with previously known processes of the modification of FS surfaces:

They are usable in repeated separations.

They allow protein separations to be accomplished with very high efficiencies and an excellent peak symmetry even at some higher pH values.

They show a good stability and reproducibility of the migration behavior.

Thermally fixed PVA coatings have proven to be stable under the conditions of CE.

The strong adsorption of PVA on the surfaces, strong interactions between the polymer chains through hydrogen bridges and a high chemical stability of the polyvinyl alcohol molecule are believed to be the reasons for the stability of the capillaries.

BRIEF DESCRIPTION OF THE DRAWINGS

The efficiency of such capillaries having been permanently deactivated with PVA coatings could be demonstrated also by way of the example of a separation of chiral compounds, in conjunction with the accompanying drawings, wherein:

FIG. 1 depicts the separation which occurred in Example 1 wherein buffers of pH 3.0 are employed.

FIG. 2 depicts the separation which occurred in Example 1 wherein buffers of pH 3.5 are employed.

FIG. 3 depicts the separation which occurred in Example 2 wherein lysozyme, cytochrome C, trypsin, ribonuclease A, trypsinogen and α-chymotrypsinogen are separated with a capillary thermally treated with PVA at a pH of 5.50.

FIG. 4 depicts the separation of acidic protein as set forth in Example 3.

FIG. 5 depicts the separation obtained in Example 4 wherein two carnitine derivatives are used.

FIG. 6 depicts the separation obtained in Example 5 in which two carnitine derivatives in addition to γ-cyclodextrin are separated.

FIG. 7 depicts the chiral separation of enantiomer pairs.

Example 1

In order to coat a commercially available capillary, a piece of about 2.5 m in length of an untreated "fused silica" capillary of an inner diameter (i.d.) of 50 µm or 75 µm (Manufacturer: MicroQuartz, München) was flushed with an about 5% by weight aqueous PVA solution (PVA, MW 50 000, degree of hydrolysis: 99+%, Aldrich, Steinhelm, Germany) by applying nitrogen under a pressure of about 1 MPa. Then the capillary filled with the PVA solution was slowly drained under the low pressure of 0.05 MPa. Then the capillary was thermally treated in an oil bath at a temperature of from 130° C. to 180° C. for 5 hours with a low nitrogen flow through the capillary (0.1 MPa).

Figure 1:
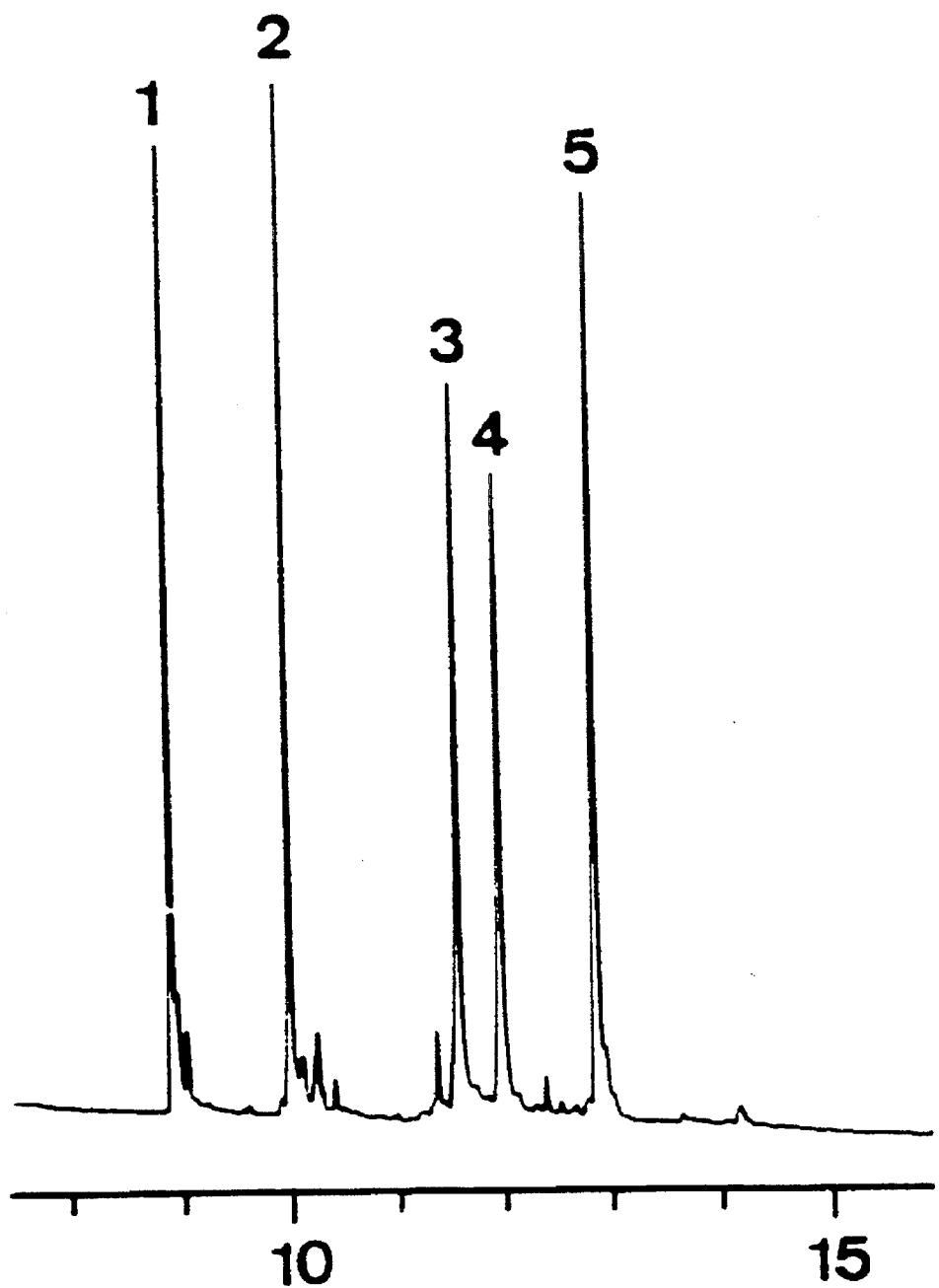
FIGS. 1 to 7 are plots showing the sharpness of separations effected with capillaries produced in accordance with the present invention, wherein the horizontal axes represent time. In particular.
Figure 2:
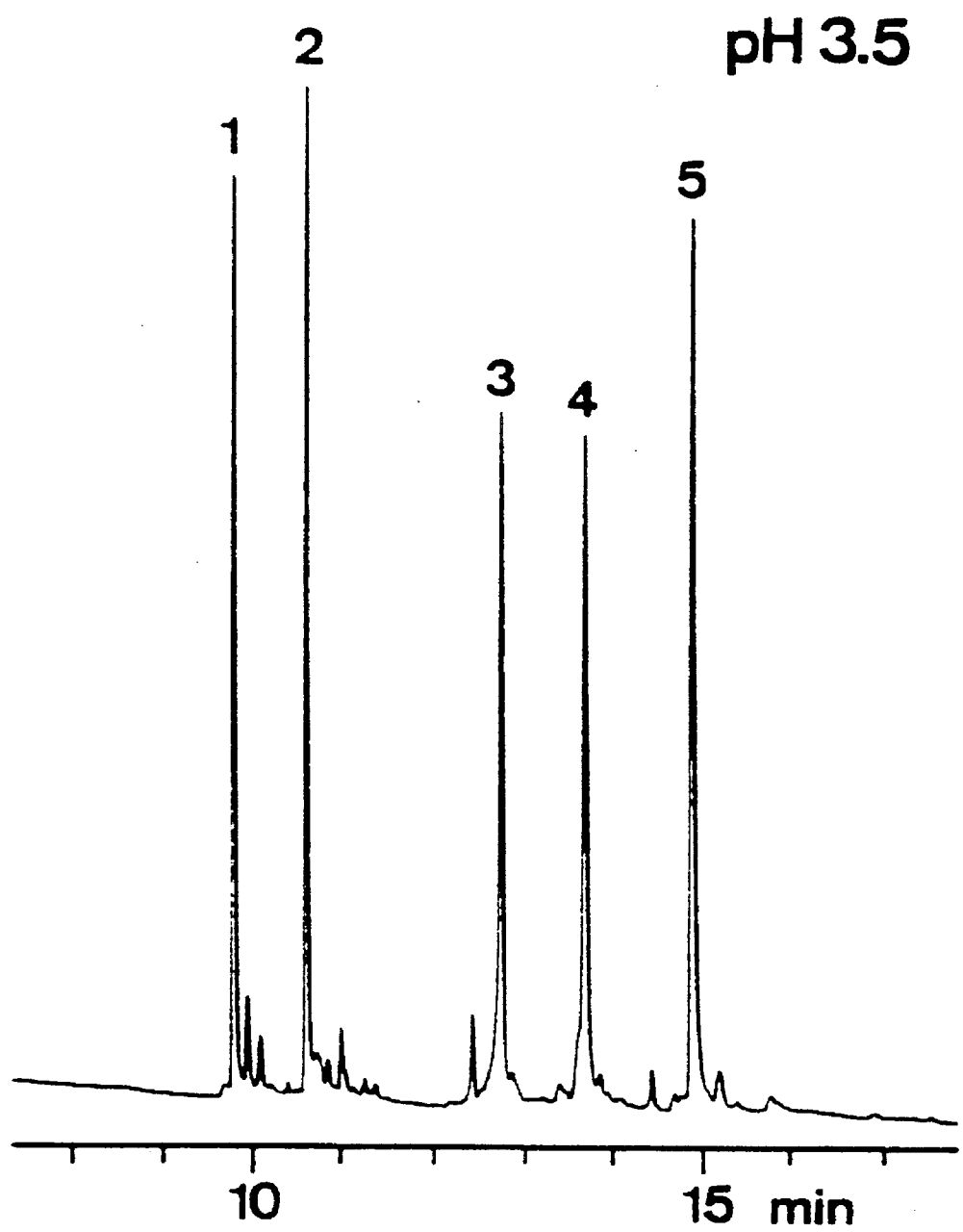

In a capillary prepared according to the procedure described above and having an effective length of 57 cm, a total length of 70 cm and an i.d. of 50 µm, a mixture comprising cytochrome C, lysozyme, trypsin, trypsinogen und α-chymotrypsinogen (0.2 mg/ml each in a buffer solution containing 50 mM of Na phosphate at pH values of 3.0 and 3.5) was separated at a field strength of 429 V/cm. The separation was effected with buffers of pH 3.0 (FIG. 1) and of pH 3.5 (FIG. 2). The efficiencies calculated from the half life widths were between 1,200,000 $m^{-1}$ for lysozyme at pH 3.0 and 710,000 $m^{-1}$ for α-chymotrypsinogen.

Sample: 1 Cytochrome C, 2 Lysozyme, 3 Trypsin, 4 Trypsinogen, 5 α-Chymotrypsinogen A; 0.2 mg/ml each.

Conditions of separation: 30 kV (429 V/cm) (A) 28 µA, (B) 29 µA; 20° C.

Buffer: 50 mM Na phosphate; (A) pH 3.0, (B) pH 3.5.

Feed: (A) 10 kV, 4 s, (B) 10 kV, 5 s.

Detection: UV 214 nm.

Example 2

In the same manner as in Example 1, the separation of lysozyme, cytochrome C, trypsin, ribonuclease A, trypsinogen and α-chymotrypsinogen was carried out using the same capillary.

Figure 3:
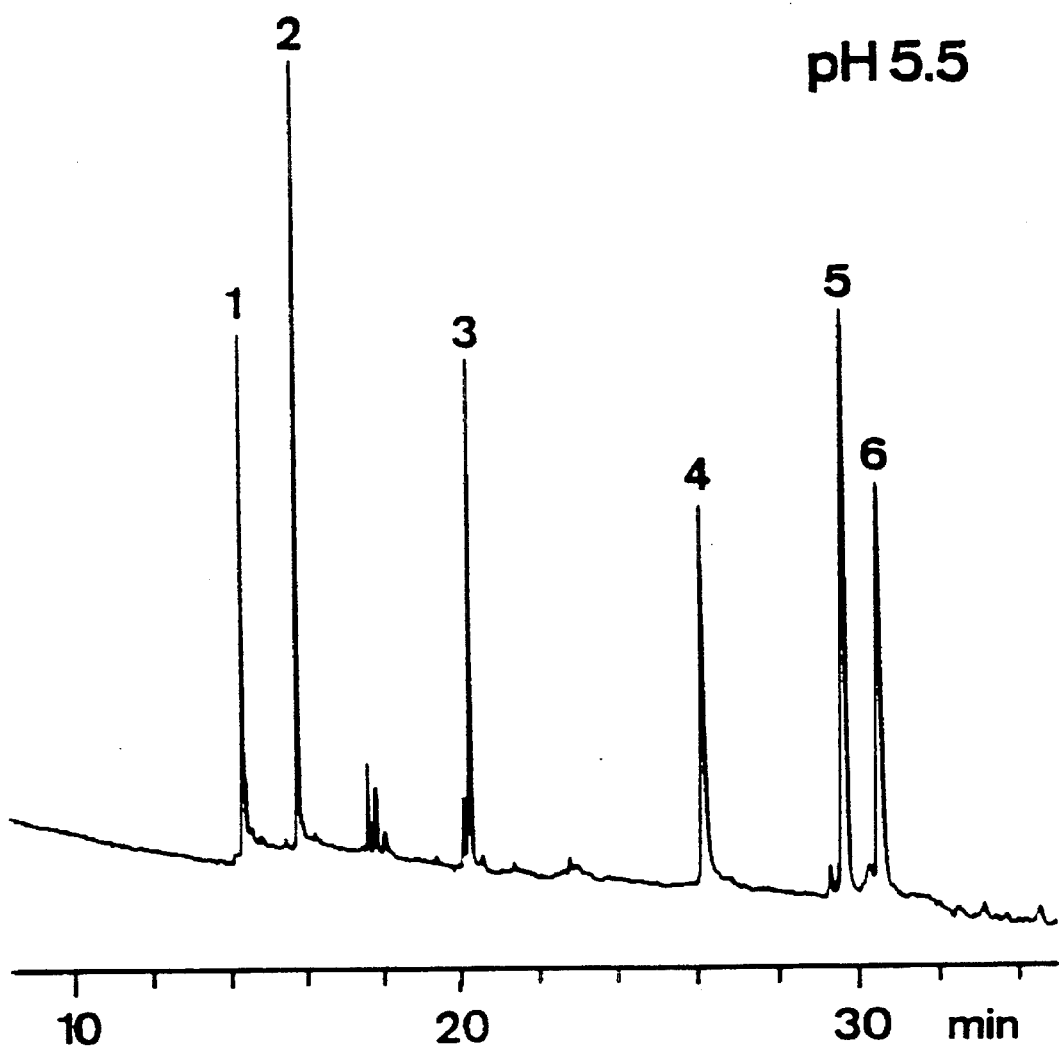

In FIG. 3 there is shown a separation of lysozyme, cytochrome C, trypsin, ribonuclease A, trypsinogen und α-chymotrypsinogen (concentrations of from 0.15 to 0.18 mg/ml in the above-mentioned buffer solution at a pH of 3.5) using a capillary coated with a thermally treated PVA at pH 5.50 (50 mM of Na phosphate, 429 V/cm). Due to the reduced mobilities of the proteins at this pH value and the low electroosmotic flow, the migration times have been increased to about two times the value. In this separation, the efficiencies are between 1,100,000 $m^{-1}$ for lysozyme and 600,000 $m^{-1}$ for α-chymotrypsinogen. The increased charge density at pH 5.5 on the surface in a capillary which has not been treated with PVA would result in a strong adsorption of the proteins. It is seen from the symmetry of the peaks that the adsorptivity of the surface of a capillary prepared by the claimed process has been much reduced.

Example 3

Figure 4:
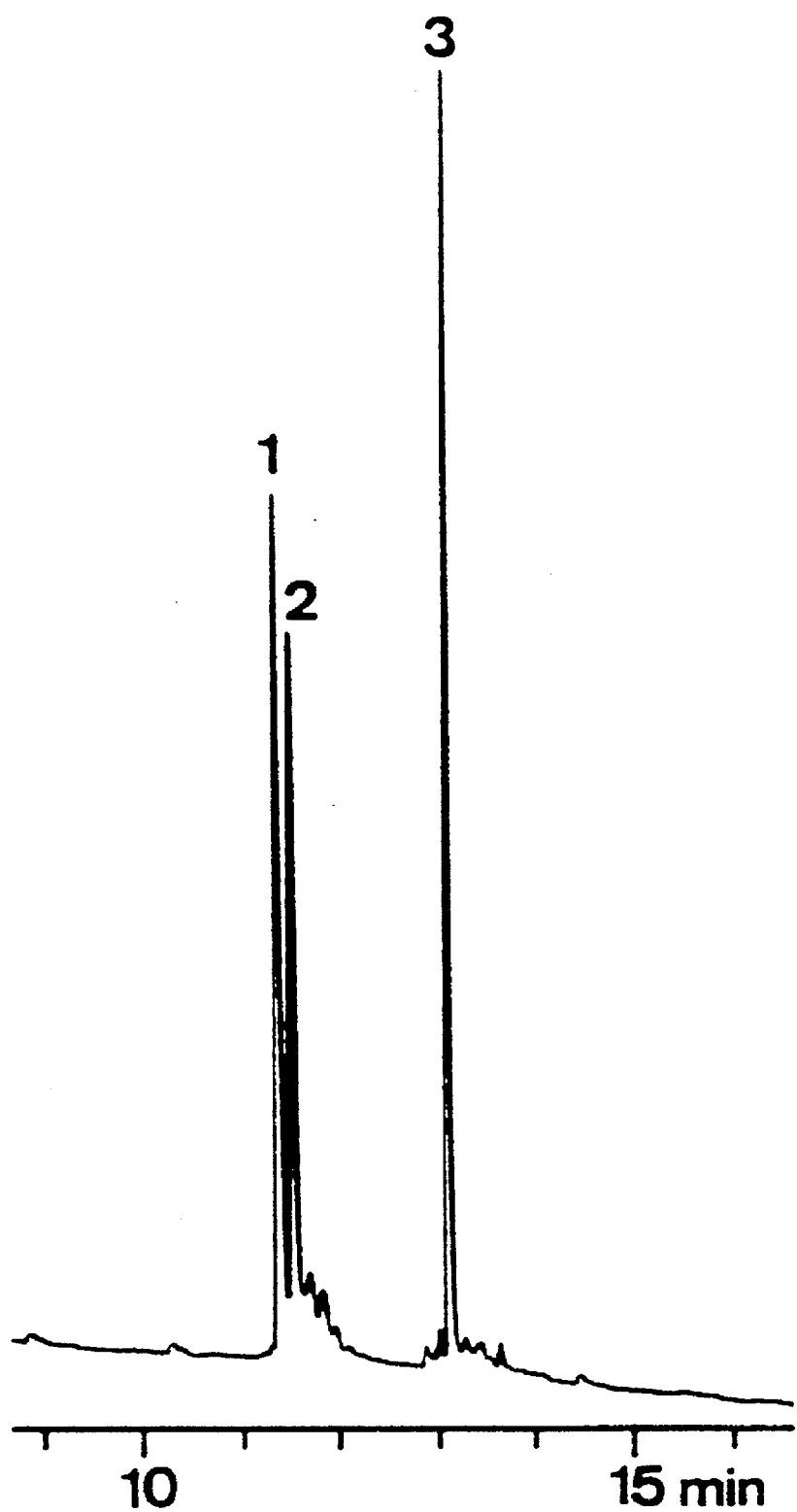

In the same manner as in Example 1, acidic proteins were separated using a capillary as described in Example 1. From FIG. 4 there are apparent the the good separations at pH 3 of the acidic proteins β-lactoglobulins A and B and α-lactalbumin, dissolved in the above-mentioned buffer, which proteins usually are strongly adsorbed.

Sample: 1 β-Lactoglobulin B, 2 β-Lactoglobulin A, 3 α-Lactalbumin; 0.3 mg/ml each.

Conditions of separation: 30 kV (429 V/cm), 23 µA; 20° C.

Buffer: 50 mM Na phosphate; pH 3.0.

Feed: 10 kV, 5 s.

Detection: UV 214 nm

Example 4

Figure 5:
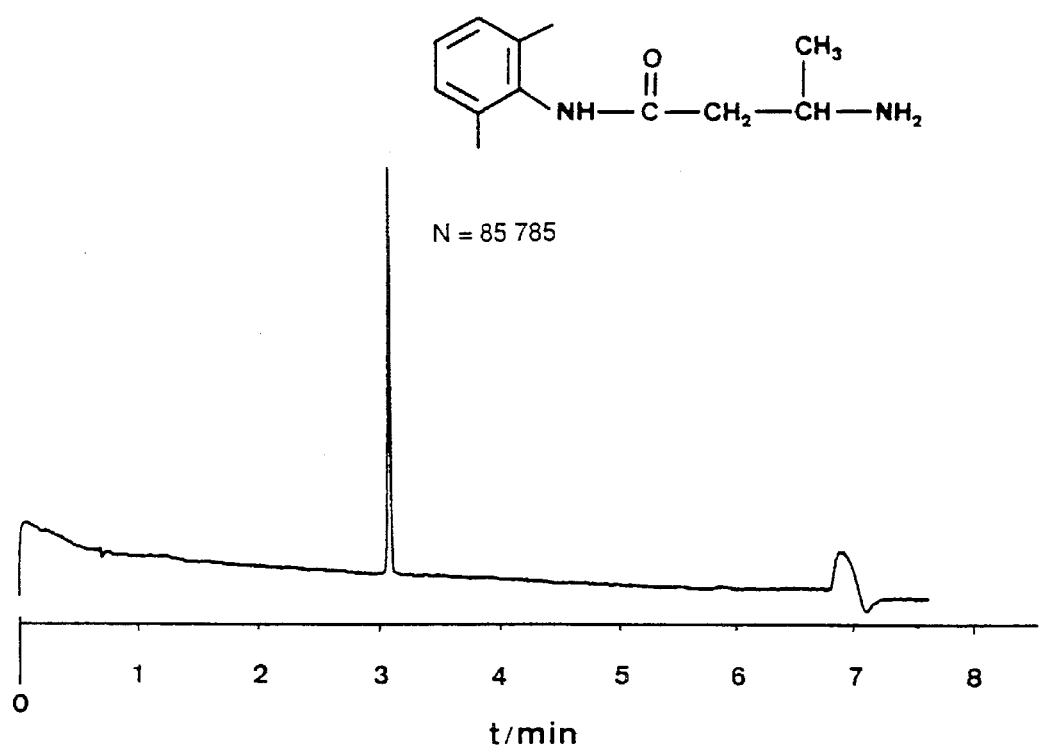
Figure 5:
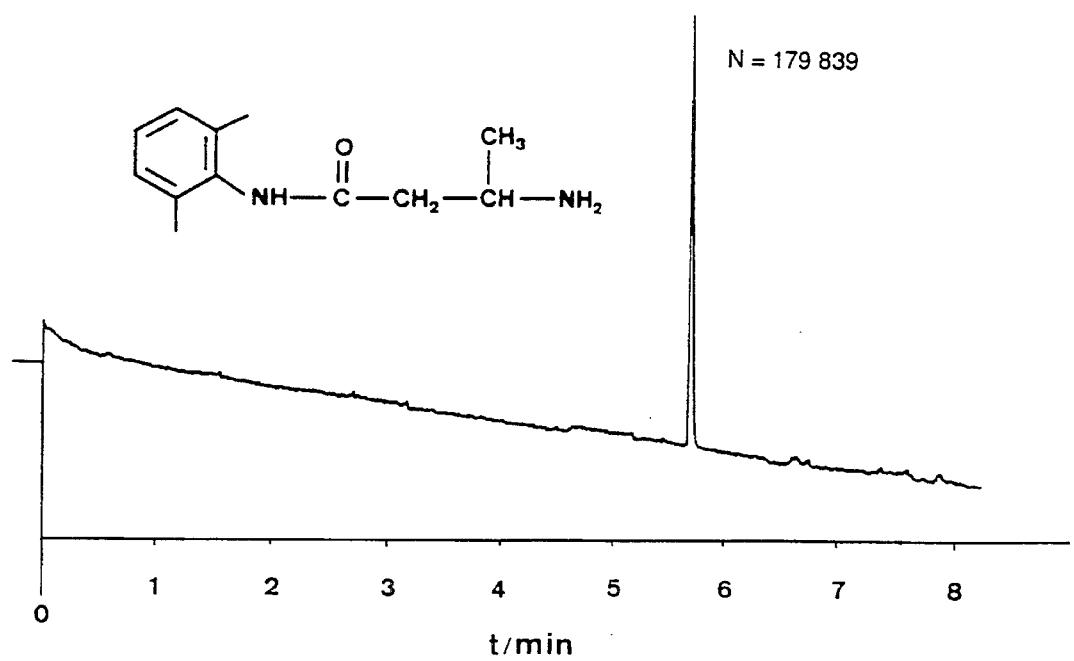

In the same manner as in Example 1, the efficiencies of the respective capillaries could be demonstrated using a tocainide derivative as an example. It will be seen from FIG. 5, that in PVA-coated capillaries also small analytes exhibit a distinct reduction of the surface adsorptivity in comparison to that on untreated capillaries. The efficiency of the peak of the tocainide derivative which is a strongly basic active substance could be increased by the PVA coating from 86,000 to 180,000 theoretical plates per one meter. The reduction in the electroosmotic flow also produces an extension of the migration time of the compound in the treated capillary.

Sample: 0.02 mg/ml in $H_2O$

Capillary: 43.2 cm of effective length, 56.7 cm of total length.
A: 50 µm i.d.; B: 50 µm i.d.

Coating: A: none; B: thermally immobilized polyvinyl alcohol, M.W. 50,000, 99% hydrolyzed, (Aldrich).

Voltage: 35 kV (617 V/cm); current 27 µA.

Buffer: 40 mM Na phosphate, pH 3.0.

Feed: hydrodynamically; ΔP: −85 mbar, 2 s.

Temperature: 20° C.

Detection: UV 210 nm.

Example 5

Figure 6:
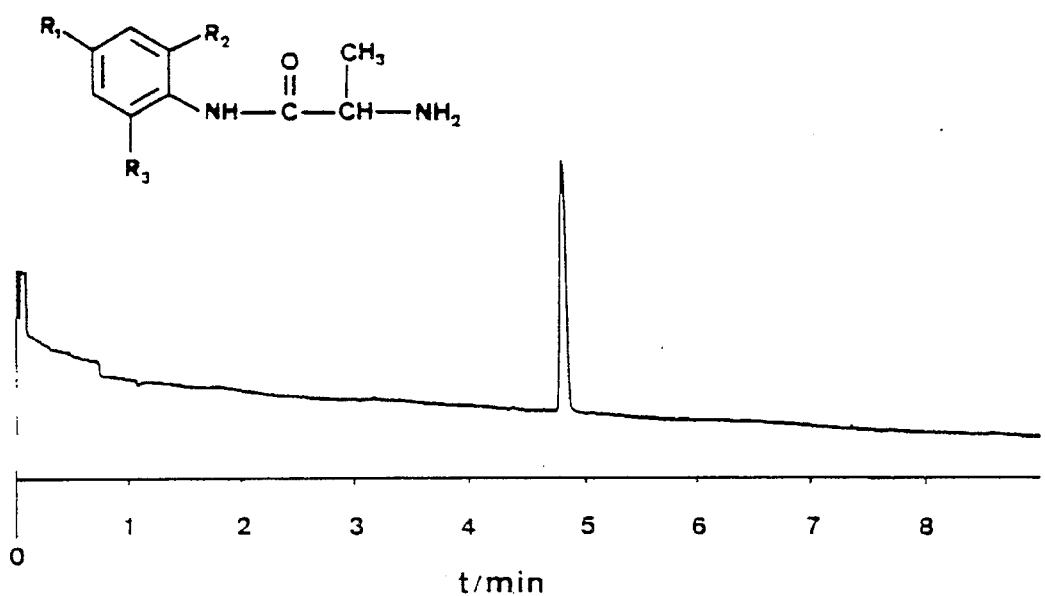
Figure 6:
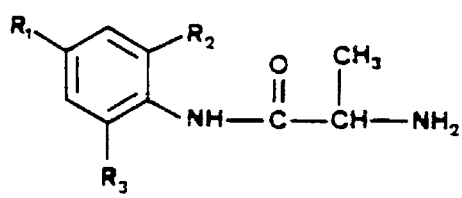
Figure 6:
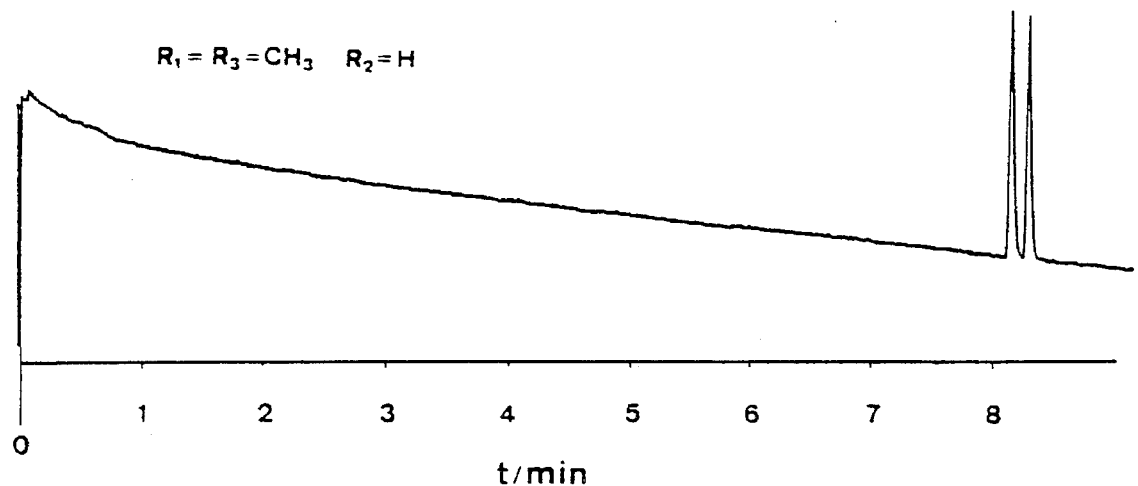

In the same manner as in Example 4, tocainide derivatives were separated with the addition of γ-cyclodextrin to the buffer. In FIG. 6 there is shown the separation of the chiral tocainides, which could be separated into enantiomers upon the addition of γ-cyclodextrin to the buffer as chiral selector. With the compound as shown here, this is possible at a sufficient resolution only in a modified capillary. The PVA coating, due to a reduction in adsorptive interactions with the capillary surface, resulted in an increased separating efficiency. In addition, the decrease of the osmotic flow results in an extended migration time of the pair of enantiomers. The cooperation of both effects causes the resolution to be increased to a separation of the base line.

Sample: 0.02 mg/ml in $H_2O$.

Capillary: 43.2 cm of effective length, 56.7 cm of total length.
A: 50 µm i.d.; B: 50 µm i.d.

Coating: A: none; B: thermally immobilized polyvinyl alcohol, M.W. 50,000, 99% hydrolyzed, (Aldrich).

Voltage: A: 35 kV; current 49 µA;
B: 35 kV; current 27 µA.

Buffer: 40 mM Na phosphate, pH 3.0.; 50 mM γ-CD.

Feed: hydrodynamically; ΔP: −85 mbar, 2 s.

Temperature: 20° C.

Detection: UV 210 nm.

Example 6

Figure 7:
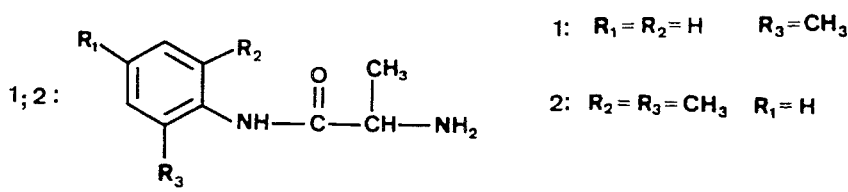
Figure 7:
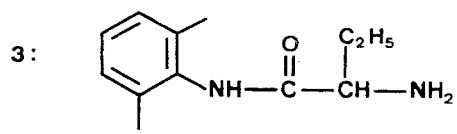
Figure 7:
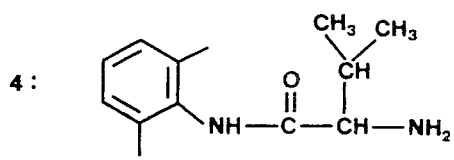
Figure 7:
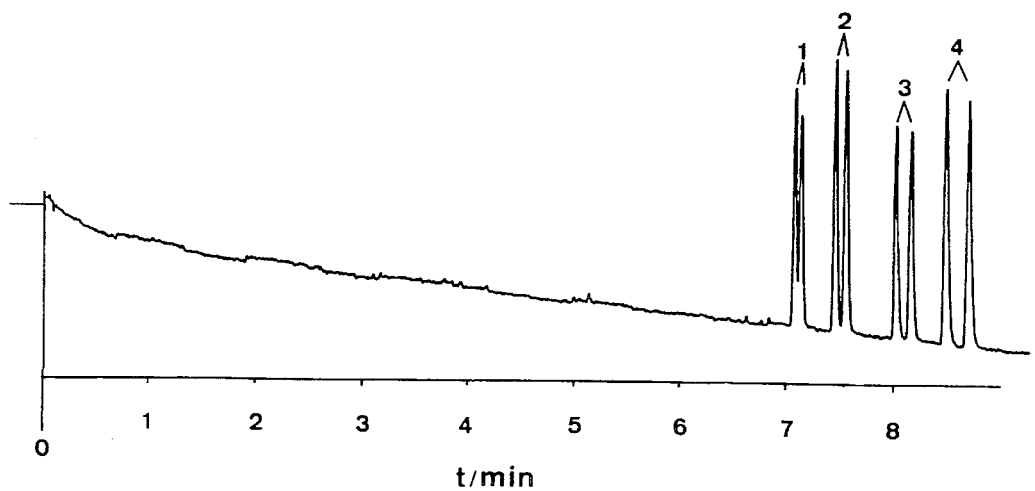

In the same manner as in Example 4, four pairs of tocainide enantiomers were separated. FIG. 7 shows the chiral separation of the enantiomer pairs.

Under the same conditions, a good separation of the four derivatives would not be possible in a capillary which has not been treated with PVA.

Sample: 0.02 mg/ml in $H_2O$

Capillary: 43.2 cm of effective length, 56.7 cm of total length; 50 µm i.d.

Coating: thermally immobilized polyvinyl alcohol, M.W. 50,000, 99% hydrolyzed, (Aldrich).

Voltage: 35 kV (617 V/cm); current 27 µA.

Buffer: 40 mM Na phosphate, pH 3.0; 50 mM γ-CD.

Feed: hydrodynamically; ΔP: −85 mbar, 2 s.

Temperature: 20° C.

Detection: UV 210 nm.

We claim:

1. A process for producing capillaries for capillary zone electrophoresis which consists of applying directly to the inner surface of a capillary an aqueous solution consisting essentially of a polar polymer, and treating the polymer to render it water-insoluble to fix it directly to the inner surface of the capillary by heat treatment.

2. A process according to claim 1, wherein after applying the polymer and before the heat treatment the capillary is drained with application of elevated pressure.

3. A process according to claim 1, wherein the heat treatment comprises heating under gas flow at atmospheric or slightly above atmospheric pressure at a temperature from 100° to 250° C. for up to 24 hours.

4. A process according to claim 1, wherein the heat treatment comprises heating under gas flow at atmospheric or slightly above atmospheric pressure at a temperature from 130° to 180° C. for 1 to 12 hours.

5. A capillary produced by the process of claim 1.

6. A process according to claim 1, wherein the polymer is polyvinyl alcohol.

7. A process according to claim 6, wherein the polyvinyl alcohol is applied as an aqueous solution of 0.5 to 10% by weight.

8. A process according to claim 6, wherein the polyvinyl alcohol is applied as an aqueous solution of 0.1 to 20% by weight.

9. A process according to claim 8, wherein the heat treatment comprises heating the capillary to a temperature above the boiling point of water under the prevailing pressure.

10. In the separation of a mixture of materials by capillary zone electrophoresis in a capillary tube, the improvement which comprises employing as the capillary, a capillary produced according to claim 9.

11. The method according to claim 10, wherein the mixture being separated contains oligonucleotides, peptides or proteins.

12. The method according to claim 10, wherein the materials are proteins, and separation is effected by passage through a series of capillaries at a pH from 3 to 10.

* * * * *